United States Patent [19]

Dorschner et al.

[11] 3,974,292
[45] Aug. 10, 1976

[54] CYANOALKYL SULFONATES FOR THE CONTROL OF FUNGUS GROWTH

[75] Inventors: Kenneth P. Dorschner, Vienna, Va.; Robert P. Johnson, Baton Rouge, La.

[73] Assignee: SCM Corporation, Cleveland, Ohio

[22] Filed: Nov. 18, 1974

[21] Appl. No.: 525,007

Related U.S. Application Data

[63] Continuation-in-part of Ser. No. 227,272, Feb. 17, 1972, abandoned, which is a continuation-in-part of Ser. No. 120,778, March 3, 1971, abandoned.

[52] U.S. Cl. .................................... 424/303
[51] Int. Cl.² ................................. A01N 9/14
[58] Field of Search ...................... 424/303, 304

[56] References Cited
UNITED STATES PATENTS

3,853,939   12/1974   Partos ................... 424/303

FOREIGN PATENTS OR APPLICATIONS

163,843   7/1964   U.S.S.R.

OTHER PUBLICATIONS

Chemical Abstracts, vol. 47 (1953), p. 2726a.
Chemical Abstracts, vol. 65 (1966), p. 8805g.
Chemical Abstracts, vol. 67 (1967), p. 11321q.

*Primary Examiner*—Albert T. Meyers
*Assistant Examiner*—Allen J. Robinson
*Attorney, Agent, or Firm*—Merton H. Douthitt; James B. Wilkens

[57] ABSTRACT

Growth of fungi can be controlled by applying to the fungi a fungicidal composition comprising an effective quantity of a cyanoalkyl sulfonate of the formula

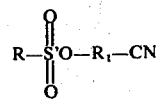

wherein $R_1$ is an alkylene group having from 1 to 4 carbon atoms and R is an aryl or arylalkyl group or an aliphatic group comprising a 1 to 12 carbon atom alkyl or cycloalkyl group at the site of attachment.

4 Claims, No Drawings

CYANOALKYL SULFONATES FOR THE CONTROL OF FUNGUS GROWTH

This application is a Continuation-In-Part of our application Ser. No. 227,272, filed Feb. 17, 1972, and now abandoned which in turn was a Continuation-In-Part of our application Ser. No. 120,778, filed Mar. 3, 1971 and now abandoned. The disclosures of both of these earlier applications are incorporated herein by reference.

Heretofore, cyanoalkyl arylsulfonates such as cyanomethyl benzenesulfonate and cyanomethyl p-toluenesulfonate have been synthesized and have been used for the preparation of organic compounds, typically amines. Additionally, compounds of the formula:

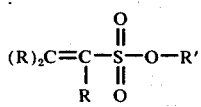

wherein R is a hydrogen or a halogen atom, and R' is an aryl group have been synthesized and disclosed as having fungicidal properties and useful for controlling growth of fungus on plants. Recently, it has also been reported German Pat. No. 1,935,293 that cyanovinyl sulfonates of the formula:

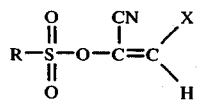

wherein R is an alkyl radical, a benzyl or phenyl radical, or substituted radical and X is hydrogen or chlorine, have acceptable fungicidal properties for making agricultural fungicides.

The agricultural fungicidal compositions of this invention have many advantageous properties. They attack a wide variety of fungi pathogenic to crop plants such as corn, cotton, oats, peas, peanuts, soybeans, sugar beets, onions, melons and the like. Representative of species of fungi which are pathogenic to crop plants and are controlled or killed by these agricultural fungicidal composition are: Rhizoctonia, Thielaviopsis, Pythium, Fusarium, Sclerotium, Aphanomyces, Urocystis, Pyrenochaeta, Glomerella, Helminthosporum, Rhizopus, Aspergillus, Phoma, Ustilage and the like.

The anti-fungal activity of the compositions is coupled with an added feature in that at effective fungicidal levels the compositions are substantially non-phytotoxic to crop plants.

Accordingly, an aspect of the invention is an improved agricultural fungicidal composition effective for controlling and killing fungi pathogenic to crop plants or plant seeds without substantially interfering with the viability of the plant or seed.

Another aspect of the invention is an improved process for killing fungi with an agricultural fungicidal composition.

Another aspect is a process for killing fungi in soils, which fungi are pathogenic to plants or plant seeds.

Another aspect is a process for killing fungi pathogenic to plant seeds without interfering with the viability of the seed.

Broadly, the compounds for making the agricultural fungicidal compositions of this invention having a broad range of fungicidal activity without being substantially phytotoxic to crop plants at effective fungicidal level as are the cyanoalkyl sulfonates represented by the formula:

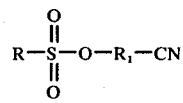

wherein $R_1$ is an alkylene group having from 1 to 4 carbon atoms and R is an aryl group or an arylalkyl group comprising an aryl group pendent from a 1 to 4 carbon atom alkylene group or an aliphatic group comprising a 1 to 12 carbon atom alkyl or cycloalkyl group at the site of attachment.

The cyanoalkyl arysulfonates set forth in our previous application Ser. No. 120,778 (1970 Series) are contemplated herein as a class of desired compounds for making an acceptable agricultural fungicidal composition. The formula of the cyanoalkyl arylsulfonates and cyanoalkyl arylalkylsulfonates contemplated here is:

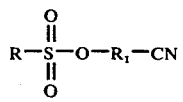

where $R_1$ is an alkylene group having from 1 to 4 carbon atoms and R is an aryl group or an arylalkyl group comprising an aryl group pendent from a 1 to 4 carbon atom alkylene group.

The aryl group contemplated are primarily the phenyl, naphthyl, anthryl and phenanthryl groups. The arylalkyl groups contemplated are primarily benzyl and phenylethyl. The aryl or arylalkyl groups can be substituted with a variety of substituent groups, substituent groups which contain no more than 4 carbon atoms being preferred. The aromatic substituted alkyl, alkenyl, alkoxy and alkoxyalkyl, carboxy and carboxyalkyl, alkoxycarbonyl and alkoxycarbonylalkyl, alkanoyloxy and alkanoyloxyalkyl, oxoalkyl, halogen and haloalkyl, and nitro and nitroalkyl derivatives are preferred. Generally, the unsubstituted or monosubstituted aryl and arylalkyl groups are used, since the fungicidal activity of the compounds sometimes decreases with increased substitution, e.g., the tri and tetra-substituted compounds, especially where alkyl groups are the substituent group. In this latter instance, substitution preferably is not to exceed mono-or di-substitution at or above the ethyl form. Examples of acceptable aromatic substituted aryl and arylalkyl groups include xylyl, toluyl, trimethylphenyl, methylanthracyl, chlorophenyl, chlorotoluyl, nitrotoluyl, ethylbenzyl, butylbenzyl and tertbutylphenyl, isopropylbenzyl, methoxyphenyl, carboxyphenyl, methoxycarbonylphenyl, acetylphenyl, etc. For reasons of efficiency and economy, a phenyl group is preferred as the R group.

The alkylene group $R_1$ can be methylene, ethylene, propylene, or butylene, or one of the isomers of the last three alkylene groups mentioned. However, compounds in which $R_1$ is methylene are particularly advantageous since such compounds appear to have a higher degree of desirable fungicidal activity.

A second class of the cyanoalkyl sulfonate compounds within the scope of this invention are cyanoalkyl aliphaticsulfonates. These compounds are represented by the formula:

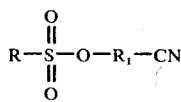

wherein $R_1$ is an alkylene group having from 1 to 4 carbon atoms and R is an aliphatic group comprising a 1 to 12 carbon atom alkyl or cycloalkyl group at the site of attachment. By an "aliphatic group", it is meant to refer to lower alkyl groups having from 1 to 12 carbon atoms, hydrocarbon isomers of the alkyl group having from 1 to 12 carbon atoms, and cyclic analogs having from 3 to 12 carbon atoms. The alkyl or cycloalkyl groups can be substituted preferably with groups which contain no more than 4 carbon atoms. The alkoxy, carboxy, alkoxycarbonyl, alkanoyloxy, oxo, halogen and nitro substituted derivatives are preferred. It has been found that those aliphatic compounds having an alkyl portion containing from about 3 to 5 carbon atoms an particularly n-butyl are most advantageous as they allow desirable latitude in formulation of agricultural fungicidal compositions.

Examples of aliphatic groups contemplated here as R are methyl, ethyl, propyl, butyl, pentyl, hexyl, octyl, nonyl, dodecyl and so forth. Isomers of such alkyl groups such as the isopropyl, isobutyl, isooctyl are also contemplated. Examples of cycloaliphatic groups include cyclopropyl, cyclohexyl, cyclopentyl, cyclohexylmethyl, chlorocyclopropyl, methylcarbonyloxycyclohexyl, and so forth. The straight chain alkyl groups are the preferred aliphatic groups.

The alkylene group $R_1$ in the cyanoalkyl aliphaticsulfonates can be methylene, ethylene, propylene, or butylene, or one of the isomers of the last three alkylene groups mentioned. However, compounds in which $R_1$ is methylene are particularly advantageous, since such compounds have a higher degree of desirable fungicidal activity.

Examples of specific cyanoalkyl arylsulfonates of the class contemplated include cyanomethyl benzenesulfonate, cyanoethyl benzenesulfonate, cyanomethyl para-toluenesulfonate, cyanomethyl parabromobenzenesulfonate, cyanomethyl tertiary-butylbenzenesulfonate, cyanomethyl 3,4-dichlorobenzenesulfonate, α-cyanoethyl benzenesulfonate, α-cyanopropyl para-toluenesulfonate, cyanomethyl p-methoxycarbonylbenzenesulfonate, cyanomethyl p-methylcarbonybenzenesulfonate, cyanomethyl p-methylcarbonyloxybenzenesulfonate, and cyanomethyl p-nitrobenzenesulfonate.

Examples of specific cyanoalkyl aliphatic sulfonates of the class contemplated include cyanomethyl methanesulfonate, cyanomethyl n-butanesulfonate, cyanomethyl 3-chloropropanesulfonate, cyanomethyl cyclohexylmethanesulfonate, cyanoethyl cyclopropanesulfonate, cyanomethyl d-10-camphorsulfonate.

By an "agriculturally acceptable carrier" it is meant to refer to a liquid organic or inorganic diluent in combination with a wetting agent or a finely divided solid carrier material, both being inert to the cyanoalkyl sulfonate compounds and not harmful to plants or seeds. Both solid and liquid agriculturally acceptable carriers are well known and widely used for applying conventional fungicides and such carries are contemplated here. Customary formulations of the fungicide and carrier are emulsions, dispersions, granular powders, pastes, and so forth. Often for marketing to the user-farmer in liquid form, the compounds are dispersed in a liquid organic carrier such as a hydrocarbon solvent containing emulsifying agent. In this form, though, the carrier is unsuited for application to farm crops. Generally, this is a concentrate form having from about 10 to 80% fungicide, the remainder being substantially inert. Proper formulation then, necessitates the addition of water to dilute the concentrate of fungicide and solvent for application. Such formulation allows wide flexibility in application to fungi in soils without substantial danger of affecting the viability of the plant, but yet effecting destruction of the fungi in soil.

Examples of organic liquids for making a marketable solution for user-farmers include lower alkanols, e.g. methanol, ethanol, isopropanol, etc., liquid hydrocarbons, e.g. paraffins having from 5 to 16 carbon atoms, e.g. hexane, pentane, kerosene, chlorinated paraffins, trichloroethylene; aromatics, e.g. benzene, naphthalene, and others mentioned in our earlier-filed application Ser. No. 120,778, previously referred to.

Solid carriers which may be used in the compositions of this invention include finely divided inorganic and organic solid materials. Suitable finely divided inorganic carriers include siliceous minerals such as clays, for example, bentonite, attapulgite, Fuller's earth, diatomaceous earth, kaolin, mica, talc, finely divided quartz, and synthetically prepared finely divided siiceous materials such as silica aerogels and precipitated and fumed silicas. Examples of finely divided solid organic materials include powdered solid non-ionic and anionic surfactants, starch, flour, sawdust, casein, gelatin, and the like.

The inert carrier, when solid, will usually contain a mixture of finely divided siliceous mineral and one or more surfactants. The amount and kind of inert carrier employed will depend upon the end use of the composition and nature of the plant pathogenic organism which it is necessary or desirable to control. By way of example, where it is desired to treat plant seeds, the carrier can be a slurried dust or an adherent powder having the cyanoalkyl sulfonate compound sorbed thereon. Conversely, where it is desired to treat soils, the composition generally is made into a wettable powder, a liquid spray or a granular formulation and applied.

The amount of inert solid or liquid carrier employed in the compositions of this invention may vary considerably depending upon the end use of the composition. When the composition is to be applied to fungus infested soil, the proportion of fungicide in the carrier should be designed to facilitate the application of an effective amount usually expressed in pounds per acre of the active material i.e., the cyanoalkyl sulfonate, to the fungi in the soil. Generally, the concentration here is about 0.05 to 10% by weight.

The amount of composition which may be employed to contact in the soil can vary widely depending upon the amounts and kinds of plant pathogens which are in the soil and the type of soil treated. Generally, this will vary in an amount of from between about 0.6 to about 100 pounds of composition per acre of soil. If less than about 0.6 pounds per acre is employed, there is some danger that not all of the fungi will be killed. Although more than 100 pounds per acre may sometimes be employed, such amounts are economically disadvantageous and there is some danger insofar as certain plants are concerned of excessive amounts of the compositions exhibiting mild phytotoxicity to the plants.

The contact of the fungi in the soil can be effected in a variety of ways and will depend upon whether the composition is in liquid or solid form. Where the composition is in liquid form, contact can be effected with a conventional spray such as those commonly employed in the agricultural pesticide field. If the composition is a finely divided particulate or granular solid, contact can be effected in much the same way as is employed when fertilizers are applied. In fact, the carrier may be a fertilizer as long as its components are inert with respect to the cyanoalkyl sulfonates of this invention.

When the compositions of this invention are used to treat crop plant seeds, contact of the seeds can preferably be done by tumbling the seeds with a powdered composition in a mixer to insure intimate contact of the fungicidal composition with the seeds.

When seeds are to be treated, the amount of composition will vary from about 0.2 to about 4% based on the weight of the seeds. The amount of composition employed will depend upon the size of the seeds and, therefore, the surface area thereof and the higher amounts on a weight basis will be employed where the size of the particular plant seed is small, the lower amounts being employed where the size of the plant seed is large. If less than about 0.2% of composition is employed, there is some danger that the seeds will not be adequately protected against attack by fungi. If more than about 4% of composition is employed there is some danger insofar as certain plant species are concerned that injury to the plant may occur during the germination of the seed.

Where the surfaces of seeds are to be treated, a powdered composition may be employed and the powdered composition used to dust at least a portion of the surfaces of the seeds will usually contain larger amounts of the cyanoalkyl sulfonate than the compositions which are to be applied to the soil. Usually from about 5 to 15% and often up to 25% compound by weight is sorbed onto the solid carrier surface. Compositions containing as much as 50% by weight of the cyanoalkyl sulfonate can be used in treating plant seeds, as illustrated by Example IV below.

Synthesis of the cyanomethyl sulfonates can be done in conventional manner similar to the synthesis of cyanomethyl sulfonate compounds which are known. Typically, the synthesis proceeds by reacting an organosulfonyl chloride; e.g., benzenesulfonyl chloride, with formaldehyde and alkali metal cyanide at about room temperature (70° F.), thereby forming cyanomethyl benzenesulfonate. Cyanomethyl aliphaticsulfonates are similarly produced by reacting an aliphaticsulfonyl chloride with formaldehyde and an alkali metal cyanide.

Various alkylene radicals, designated at $R_1$ in the cyanoalkyl sulfonate formulas, can be introduced in place of the methylene radical by reacting with appropriate alkyl aldehydes in place of formaldehyde. The resulting structure then will appear as a methylene bridge between an oxygen and cyano group with an alkyl portion pendant from the methylene radical. Such aldehydes for this reaction are acetaldehyde, proprionaldehyde and butyraldehyde. Alternatively, alkylene groups can be introduced by reacting appropriate cyanoalkyl alcohols with the organosulfonyl chloride. However, the compounds where $R_1$ is an alkylene radical other than methylene are not as desirable because fungicidal activity drops off substantially with increasing carbon content.

EXAMPLE I

A quantity of standard soil was sterilized in the conventional manner, with methyl bromide and was inoculated with the organisms shown in Table I below. The composition consisting of the compound dispersed in water and a surfactant was then applied to the soils as a drench in the amounts indicated in Table I. The active compound of the compositions employed are also listed in Table I. The soil was inoculated by admixing 10% of a culture which had been prepared and maintained by adding the particular fungus organism to a sterile soil to which had been added 20% by weight based on the weight of the soil of cornmeal. The inoculated soil samples were placed in individual disposable 4 inches square by 6 inches deep containers and placed in a greenhouse, after being treated with cyanomethyl p-toluenesulfonate and cyanomethyl benzenesulfonate in the amounts indicated in Table I. Three control groups consisting respectively of soil treated with a standard fungicidal agent (1-chloro-2-nitro-propane), untreated sterile woil and inoculated soil served as controls. The surface of the soil in the containers was observed for five days and the percent of surface of the soil in each container covered with mycelial growth was observed in each instance.

The soil treatment level was respectively 100, 50, and 25 parts per million based on the weight of the soil. The results are shown in Table I. The untreated inoculated soils were completely covered with mycelial growth within five days. The 1-chlor-2 nitropropane was not effective against *Sclerotium rolfsii* and *Fusarium oxysporum* at levels of 50 and 25 parts per million. The two test compositions were effective against all organisms at 100 parts per million and partially to completely effective against other organisms as shown in Table I. The above example demonstrates the effectiveness of the test compositions against four fungus organisms which are pathogenic to plants and cause crop damage.

TABLE I

| Chemical Treatment | Dose ppm of Soil | Mycelial Growth — % Container Area Covered | | | |
| --- | --- | --- | --- | --- | --- |
| | | Pythium irregulars | Rhizoctonia solani | Sclerotium rolsii | Fusarium oxysporum |
| Cyanomethyl P-toluene sulfonate | 100 | 10 | 10 | 10 | 30 |
| " | 50 | 10 | 40 | 20 | 70 |
| " | 25 | 30 | 70 | 50 | 100 |

TABLE I-continued

| Chemical Treatment | Dose ppm of Soil | Mycelial Growth — % Container Area Covered | | | |
|---|---|---|---|---|---|
| | | Pythium irregulars | Rhizoctonia solani | Sclerotium rolsii | Fusarium oxysporum |
| Cyanomethyl benzene-sulfonate | 100 | 10 | 0 | 0 | 0 |
| " | 50 | 20 | 20 | 40 | 40 |
| " | 25 | 60 | 70 | 70 | 70 |
| 1-chloro-2-nitro-propane | 100 | 20 | 10 | 50 | 30 |
| " | 50 | 30 | 30 | 100 | 100 |
| " | 25 | 50 | 60 | 100 | 100 |
| Sterile Soil | — | 0 | 0 | 0 | 0 |
| Inoculated Soil | — | 100 | 100 | 100 | 100 |

EXAMPLE II

The experiment described in Example I was repeated with cyanomethyl P-toluenesulfonate and the controls. The results are set forth in Table II and show that compositions containing cyanomethyl P-toluenesulfonate are superior to the standard 1-chlor-2-nitropropane with respect to fungicidal effectiveness and absence of phytotoxicity.

TABLE II

| Chemical Treatment | Dose, ppm of Soil | Plant Stand — % Sterile Soil Check Pythium irregulars English Peas |
|---|---|---|
| Cyanomethyl P-toluene sulfonate | 100 | 94 |
| " | 50 | 101 |
| " | 25 | 59 |
| 1-chlor-2-nitro-propane | 100 | 18* |
| | 100 | 18* |
| " | 50 | 76 |
| " | 25 | 94 |
| Sterile Soil | — | 85** |
| Inoculated Soil | — | 0 |

*Phytotoxic
**Absolute percentage surviving in sterile soil without treatment; the other figures represent survival rate relative to this control.

EXAMPLE III

The procedures of Examples I and II were repeated except that beet seeds, cucumber seeds, and tomato seeds were planted in soil contaminated with Rhizoctonia solani, Sclerotium rolfsii. and Fusarium oxysporum which had been treated with compositions containing cyanomethyl P-toluenesulfonate. The cyanomethyl P-toluenesulfonate was superior to the standard compound, 1-chloro2-nitro-propane. In every instance, cyanomethyl P-toluenesulfonate protected beets, cucumbers, and tomatoes against attack by the three pathogens as shown in Table III.

TABLE III

| Chemical Treatment | Dose ppm of Soil | Plant Stand — % Sterile Soil Check | | |
|---|---|---|---|---|
| | | Rhizoctonia solani Beets | Sclerotium rolfsii Cucumbers | Fusarium oxysporum Tomatoes |
| Cyanomethyl p-toluene sulfonate | 100 | 87 | 106 | 94 |
| " | 50 | 100 | 106 | 88 |
| " | 25 | 67 | 94 | 88 |
| 1-chloro-2-nitro-propane | 100 | 13* | 18 | 24* |
| " | 50 | 100 | 18 | 71 |
| " | 25 | 67 | 0 | |
| Sterile Soil | — | 75 | 85 | 85** |
| Inoculated Soil | — | 10 | 5 | 40 |

*Phytotoxic
**Absolute percentage surviving in sterile soil without treatment; the other figures represent survival rate relative to this control.

EXAMPLE IV

A formulation consisting of 50 weight parts of cyanomethyl benzene sulfonate and montmorillonite clay were prepared and dusted on beet seeds. The procedure of Example III was repeated, except that the treated beet seeds were planted in soil that had been contaminated with Rhizoctonia solani and the standard control employed was N-trichloromethyl thio-4-cyclohexene-1,2-dicarboximide. The beet seeds were mixed in such a way as to provide seeds treated with 4, 2, and 1 ounce per nushel respectively of the formulated composition. The results, which are given in Table IV show that the cyanomethyl benzenesulfonate composition was substantially identical to that of the standard fungicidal agent used as control.

TABLE IV

| Chemical Treatment | Dose — Oz./ Bu. 50% Formulation | Plant Stand — % Sterile Soil Check Rhizoctonia solani Beets |
|---|---|---|
| Cyanomethyl benzene-sulfonate | 4 | 88 |
| " | 2 | 88 |
| " | 1 | 70 |
| N-trichloro-methyl thio-4-cyclohexene- | | |

TABLE IV-continued

| Chemical Treatment | Dose — Oz./ Bu. 50% Formulation | Plant Stand — % Sterile Soil Check Rhizoctonia solani Beets |
|---|---|---|
| 1,2-dicarbox-imide | 4 | 88 |
| " | 2 | 94 |
| " | 1 | 59 |
| Sterile Soil | — | 85** |
| Inoculated Soil | — | 20 |

**Absolute percentage surviving in sterile soil without treatment; the other figures represent survival rate relative to this control.

In the foregoing examples I through IV, when compositions containing cyanoethyl benzenesulfonate, cyanopropyl benzenesulfonate, cyanoethyl P-toluenesulfonate and cyanopropyl P-toluenesulfonate are employed in place of the materials employed in those examples, substantially the same results are obtained as were obtained in those examples. When compositions containing cyanomethyl naphthylenesulfonate and cyanomethyl xylenesulfonate are employed in place of the compounds employed in Examples I through IV, substantially similar results were obtained as were obtained in those examples.

EXAMPLE V

The compounds, cyanomethyl butanesulfonate, cyanomethyl methanesulfonate, cyanomethyl chloropropanesulfonate, cyanomethyl octanesulfonate, cyanomethyl α-toluenesulfonate and cyanomethyl benzenesulfonate were synthesized and evaluate for their effectiveness as fungicides, as well as for their phytotoxicity to crop plants. Additionally, the results were compared with Lanstan* (1-chloro-2-nitropropane), a commercially available fungicide which was tested in the same manner.

* A trademark of FMC Corporation

The above compounds were tested and evaluated in precisely the same manner as those set forth in Example I and II of this application. Table V represents the results of the compounds and their effectiveness in controlling mycelial growth for four types of fungus as shown. Table VI represents the percent stand with each of the compounds for appropriate plants.

TABLE V

| Chemical Treatment | Dose ppm of Soil | Mycelial Growth — % Container Area Covered | | | |
|---|---|---|---|---|---|
| | | Pythium irregulars | Rhizoctonia solani | Sclerotium rolfsil | Fusarium oxysporum |
| Cyanamethyl butane sulfonate | 100 | 0 | 0 | 0 | 10 |
| Cyanomethyl methane sulfonate | 100 | 90 | 10 | 0 | 0 |
| Cyanomethyl chloropropane sulfonate | 100 | 100 | 10 | 0 | 10 |
| Cyanomethyl octane sulfonate | 100 | 30 | 100 | 40 | 20 |
| Cyanomethyl α-toluene sulfonate | 100 | 80 | 10 | 10 | 10 |
| Cyanomethyl benzene-sulfonate | 100 | 70 | 20 | 10 | 10 |
| Lanstan* | 100 | 10 | 10 | 20 | 30 |
| Sterile Soil | — | 0 | 0 | 0 | 0 |
| Inoculated Soil | — | 100 | 100 | 100 | 100 |

*A Trademark of FMC Corporation

TABLE VI

| Chemical Treatment | Dose ppm of Soil | Plant Stand — % Sterile Soil Check | | | |
|---|---|---|---|---|---|
| | | Pythium irregulars English Peas | Rhizoctonia solani Beets | Sclerotium rolfsil Cucumbers | Fusarium oxysporum Tomatoes |
| Cyanomethyl butyl-sulfonate | 100 | 65 | 75 | 60 | 60 |
| Cyanomethyl methyl-sulfonate | 100 | 10 | 10 | 95 | 65 |
| Cyanomethyl chloropropyl-sulfonate | 100 | 50 | 85 | 70 | 20 |
| Cyanomethyl octyl-sulfonate | 100 | 60 | 35 | 80 | 40 |

TABLE VI-continued

| Chemical Treatment | Dose ppm of Soil | Plant Stand — % Sterile Soil Check | | | |
| --- | --- | --- | --- | --- | --- |
| | | Pythium irregulars English Peas | Rhizoctonia solani Beets | Sclerotium rolfsii Cucumbers | Fusarium oxysporum Tomatoes |
| Cyanomethyl benzyl-sulfonate | 100 | 65 | 95 | 30 | 30 |
| Cyanomethyl benzene-sulfonate | 100 | 35 | 65 | 30 | 10 |
| Lanstan* | 100 | 60 | 45 | 0 | 20 |
| Sterile Soil | — | 90** | 95** | 95** | 95** |
| Inoculated Soil | — | 15 | 45 | 0 | 20 |

*A Trademark of FMC Corporation
**Absolute percentage surviving in sterile soil without treatment; the other figures represent survival rate relative to this control.

What is claimed is:

1. A process for controlling the growth of fungi in soil, which comprises applying to said fungi an effective amount of a fungicidal composition comprising an agriculturally acceptable carrier and a cyanoalkyl sulfonate represented by the formula

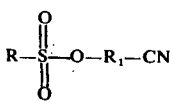

wherein $R_1$ is an alkylene group having from 1 to 4 carbon atoms and R is an unsubstituted or substituted 1 to 12 carbon atom alkyl or cycloalkyl group wherein the substituents can be alkoxy, carboxy, alkoxycarbonyl, alkanoyloxy, oxo, halogen or nitro groups containing not more than 4 carbon atoms each.

2. The process of claim 1 wherein said cyanoalkyl sulfonate is cyanomethyl n-butanesulfonate.

3. A process for treating plant seeds with a fungicidal composition which comprises applying to said seed an amount of said fungicidal composition effective for controlling the growth of fungi, wherein said fungicidal composition comprises an agriculturally acceptable carrier and a cyanoalkyl sulfonate represented by the formula

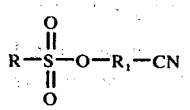

wherein $R_1$ is an alkylene group having from 1 to 4 carbon atoms and R is an unsubstituted or substituted 1 to 12 carbon atom alkyl or cycloalkyl group wherein the substituents can be alkoxy, carboxy, alkoxycarbonyl, alkanoyloxy, oxo, halogen or nitro groups containing not more than 4 carbon atoms each.

4. The process of claim 3 wherein said cyanoalkyl sulfonate is cyanomethyl n-butanesulfonate.

* * * * *